(12) United States Patent
Akagane

(10) Patent No.: US 10,874,419 B2
(45) Date of Patent: Dec. 29, 2020

(54) SURGICAL INSTRUMENT

(71) Applicant: OLYMPUS CORPORATION, Hachioji (JP)

(72) Inventor: Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 92 days.

(21) Appl. No.: 16/040,973

(22) Filed: Jul. 20, 2018

(65) Prior Publication Data
US 2018/0333171 A1 Nov. 22, 2018

Related U.S. Application Data

(63) Continuation of application No. PCT/JP2016/051543, filed on Jan. 20, 2016.

(51) Int. Cl.
*A61B 17/32* (2006.01)
*A61B 18/14* (2006.01)
(Continued)

(52) U.S. Cl.
CPC .. *A61B 17/320092* (2013.01); *A61B 17/3211* (2013.01); *A61B 18/1442* (2013.01); *A61B 18/1206* (2013.01); *A61B 2017/00853* (2013.01); *A61B 2017/320073* (2017.08); *A61B 2017/320074* (2017.08); *A61B 2017/320078* (2017.08); *A61B 2017/320095* (2017.08); *A61B 2018/0013* (2013.01); *A61B 2018/0063* (2013.01); *A61B 2018/00107* (2013.01); *A61B 2018/00142* (2013.01); *A61B 2018/00148* (2013.01); *A61B 2018/00589* (2013.01); *A61B 2018/00601* (2013.01); *A61B 2018/126* (2013.01); *A61B 2018/1253* (2013.01);
(Continued)

(58) Field of Classification Search
CPC ........ A61B 17/320092; A61B 17/3211; A61B 2017/320073; A61B 2017/320074; A61B 2017/320095; A61B 2017/320078; A61B 2017/00853; A61B 2018/00107; A61B 2018/0013; A61B 2018/00142; A61B 2018/00148; A61B 2018/00589; A61B 2018/00601; A61B 2018/0063
See application file for complete search history.

(56) References Cited

U.S. PATENT DOCUMENTS

2005/0154385 A1 7/2005 Heim et al.
2009/0143806 A1 6/2009 Witt et al.
(Continued)

FOREIGN PATENT DOCUMENTS

CN 101883530 A 11/2010
JP H10-202372 A 8/1998
(Continued)

OTHER PUBLICATIONS

Jul. 24, 2018 International Preliminary Report on Patentability issued in International Patent Application PCT/JP2016/051543.
(Continued)

*Primary Examiner* — Ashley L Fishback
(74) *Attorney, Agent, or Firm* — Oliff PLC

(57) ABSTRACT

A surgical instrument includes an end effector with a surface made of amorphous titanium oxide, and a film resin covering the surface and chemically bonding to the surface.

13 Claims, 3 Drawing Sheets

(51) Int. Cl.
  *A61B 17/3211* (2006.01)
  *A61B 18/12* (2006.01)
  *A61B 18/00* (2006.01)
  *A61B 17/00* (2006.01)
  *A61L 31/02* (2006.01)
  *A61L 31/10* (2006.01)
  *A61L 31/14* (2006.01)
  *C25D 11/02* (2006.01)

(52) U.S. Cl.
  CPC ............ *A61L 31/028* (2013.01); *A61L 31/10* (2013.01); *A61L 31/14* (2013.01); *A61L 2400/10* (2013.01); *C25D 11/022* (2013.01)

(56) References Cited

U.S. PATENT DOCUMENTS

2009/0306552 A1  12/2009  Furuzono et al.
2012/0029514 A1  2/2012   Fairbourn et al.
2018/0353658 A1* 12/2018  Murano .................. A61L 31/10

FOREIGN PATENT DOCUMENTS

| JP | 2004-143417 A | 5/2004 |
| JP | 2010-012218 A | 1/2010 |
| JP | 2011-505198 A | 2/2011 |
| JP | 2012-101160 A | 5/2012 |

OTHER PUBLICATIONS

Apr. 19, 2016 International Search Report issued in International Patent Application PCT/JP2016/051543.
Sep. 9, 2019 Extended Search Report issued in European Patent Application No. 16886293.6.
May 8, 2020 Office Action issued in Chinese Patent Application No. 201680079679.5.

* cited by examiner

SURGICAL INSTRUMENT

CROSS-REFERENCE TO RELATED APPLICATIONS

This application is a Continuation Application of PCT Application No. PCT/JP2016/051543, filed Jan. 20, 2016, the entire contents of all of which are incorporated herein by reference.

FIELD

The present invention relates to a surgical instrument that performs treatment on body tissue with various energies.

BACKGROUND OF THE INVENTION

As disclosed in Jpn. Pat. Appln. KOKAI Publication No. 2011-505198 (Patent Literature 1), there is an ultrasonic surgical blade that performs treatment on body tissue using ultrasonic waves. This ultrasonic surgical blade includes a lubricating coating material on a part of the outer surface of the main body.

As disclosed in Jpn. Pat. Appln. KOKAI Publication No. 2012-101160 (Patent Literature 2), there is a medical ultrasonic device that performs treatment on body tissue using ultrasonic waves. In this medical ultrasonic device, an insulator portion is provided on the outer peripheral surface of the vibration output section. The insulator portion prevents a current induced in the vibrator body from flowing into the vibrated body.

CITATION LIST

Patent Literature

[Patent Literature 1] Jpn. PCT National Publication No. 2011-505198

[Patent Literature 2] Jpn. PCT National Publication No. 2012-101160

SUMMARY

In general, a surgical instrument has an assumed number of times of use per surgical operation, and various designs are made so as to maintain a level of durability exceeding this number. On the other hand, surgical instruments are required to be used under more severe conditions than usual depending on the use of surgical instruments, and further improvement of durability of surgical instruments is required.

DETAILED DESCRIPTION

An embodiment of an energy treatment device of the present invention will be described with reference to FIGS. 1 to 4.

Figure 1:
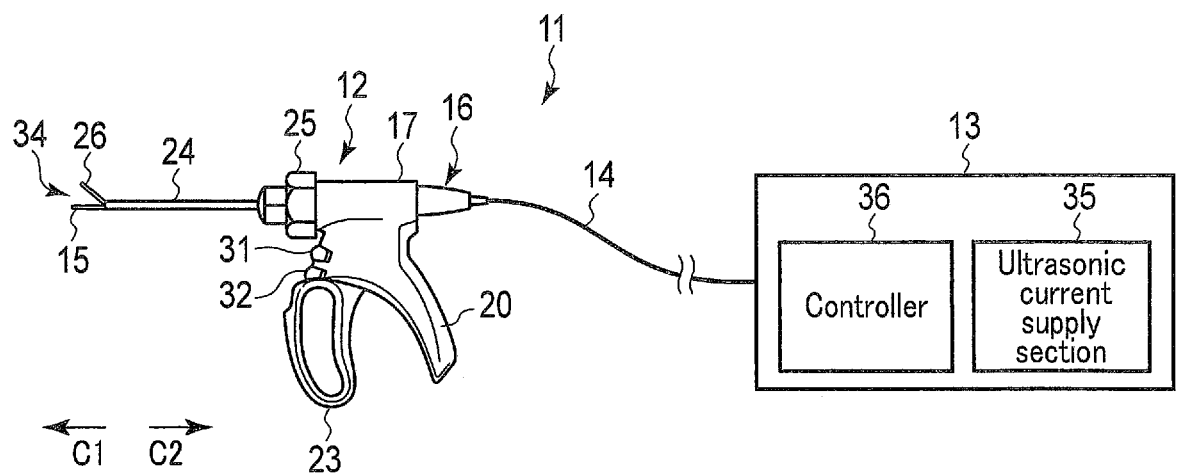
FIG. 1 is a schematic diagram showing the overall configuration of the surgical instrument according to an embodiment.
Figure 2:
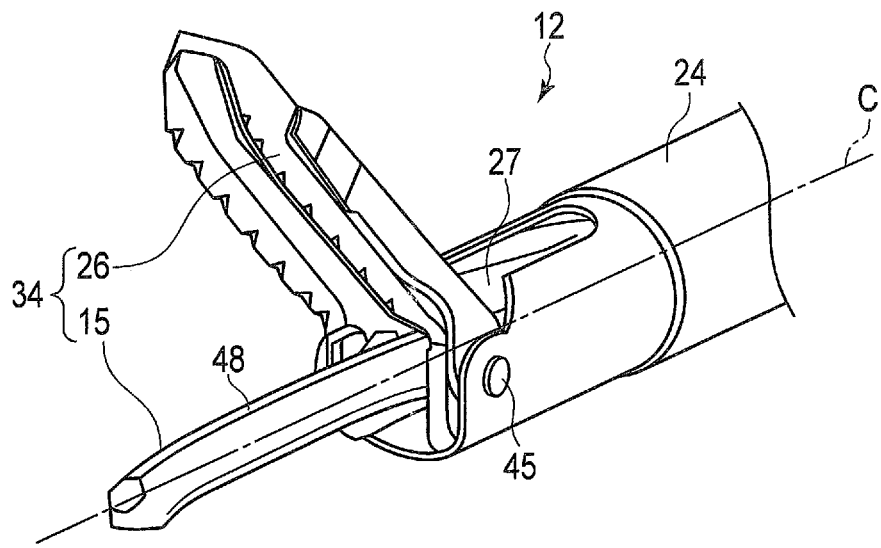
FIG. 2 is a perspective view showing the end effector of the handpiece of the surgical instrument shown in FIG. 1.
Figure 3:
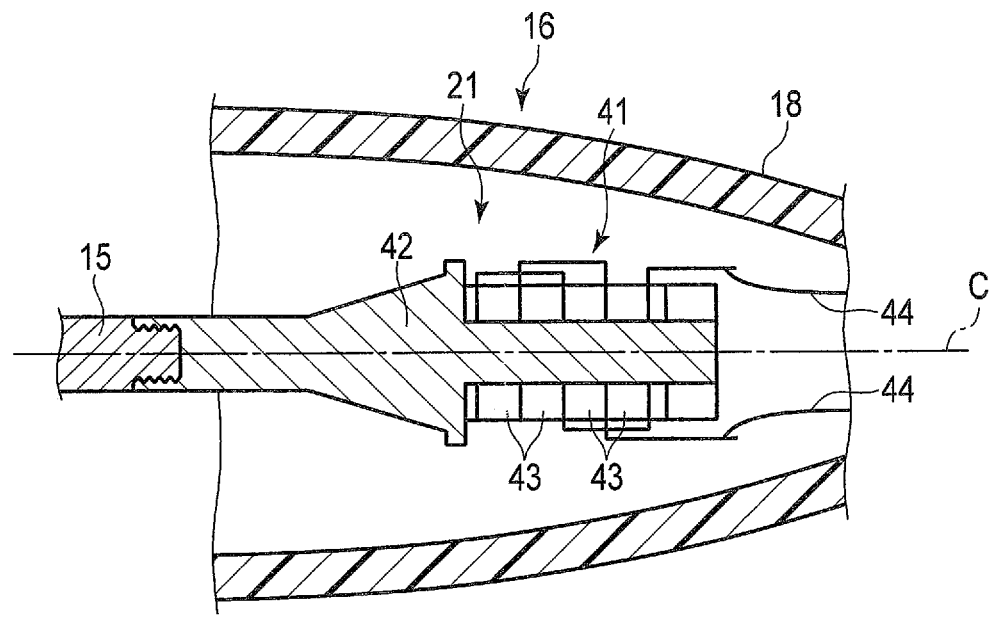
FIG. 3 is a cross-sectional view showing the oscillator unit of the surgical instrument shown in FIG. 1.

As shown in FIGS. 1 to 3, a surgical instrument 11 (medical device) includes a handpiece 12, a power supply unit 13, a cable 14 connecting the handpiece 12 and the power supply unit 13, and an oscillator unit 16 (transducer) that supplies ultrasonic vibrations for making a probe 15 of the handpiece 12 resonate.

The oscillator unit 16 includes a case 18 detachable from the handpiece 12 (housing 17) and a vibration generator 21 held in the case 18. In addition, the surgical instrument disclosed in the present embodiment includes a handpiece 12 and an oscillator unit 16. In the present embodiment, one of the two directions parallel to the central axis C (longitudinal axis) of the probe 15 is defined as a distal direction C1, and the direction opposite to the distal direction C1 is defined as a proximal direction C2.

The handpiece 12 includes a housing 17 forming a part of the outer shell, a grip portion 20 projecting like a rod from the housing 17, a movable handle 23 rotatably attached to the housing 17 with respect to the grip portion 20, stick-shaped probe 15 (vibration transmission member) connected (fixed) to the vibration generator 21, a cylindrical sheath 24 attached to the housing 17 to cover the circumference of the probe 15, and a knob 25 fixed to the sheath 24, a jaw 26 provided rotatably with respect to the probe 15 and the sheath 24, a cylindrical movable pipe 27 provided inside the sheath 24 and moved forward and backward when opening and closing the jaw 26, a first button 31 and second button 32 provided in the housing 17 and configured to switch ultrasonic vibrations output from the vibration generator 21 on and off, and an annular seal member 33 (elastic member) interposed between the probe 15 and the movable pipe 27. The seal member 33 is made of, for example, a rubber material. In a state where the probe 15 is vibrated by transmitted ultrasonic vibrations, one of the node positions N of the ultrasonic vibrations is located at a position where the seal member 33 is disposed with respect to the longitudinal axis C direction. The probe 15 and the jaw 26 form an end effector 34 that performs treatment on body tissue.

As shown in FIG. 1, the power supply unit 13 includes an ultrasonic current supply section 35 and a controller 36 that controls the ultrasonic current supply section 35. The controller 36 can control supply of electric power from the ultrasonic current supply section 35. When the first button 31 or the second button 32 is pushed in by the doctor, the controller 36 supplies electric power (AC power) from the ultrasonic current supply section 35 to the vibration generator 21. The first button 31 located on the probe 15 side corresponds to a seal mode treatment (function) of outputting, for example, an ultrasonic energy with a reduced amplitude of ultrasonic vibrations to perform coagulation/hemostasis on body tissue. The second button 32 located on the movable handle 23 side corresponds to a cut mode treatment (function) of outputting, for example, an ultrasonic energy with an increased amplitude of ultrasonic vibrations to mainly incise body tissue.

In the present embodiment, an ultrasonic energy using ultrasonic vibrations is used as the treatment energy; however, the treatment energy is not limited to the ultrasonic energy. The treatment energy may be a high-frequency energy using a high-frequency current, a thermal energy capable of coagulating and burning off body tissue by high temperature, or an RF energy using RF (radio waves).

When the high-frequency energy is used as the treatment energy, the surgical instrument 11 can be utilized as a bipolar-type electric scalpel or a monopolar-type electric scalpel. In the case of utilizing the surgical instrument 11 as the bipolar type, the probe 15 of the end effector 34 can be used as one pole of the bipolar-type electric scalpel, and the jaw 26 of the end effector 34 can be used as the other pole of the bipolar-type electric scalpel.

In the case of utilizing the surgical instrument 11 as the monopolar-type electric scalpel, the probe 15 of the end effector 34 may be used as the monopolar-type electric scalpel, so that a high-frequency current flows between the probe 15 and a return electrode provided outside the patient's body. When the thermal energy is used as the treatment energy, it is preferable to provide a heater on the probe 15 side, for example. When the RF energy is used as the treatment energy, it is preferable to provide an RF output section on the probe 15 side, for example.

In addition, the above-described treatment energies can either be input to body tissue alone or simultaneously input to body tissue in combination. That is, a combined treatment energy of the ultrasonic energy and high-frequency current energy, a combined treatment energy of the ultrasonic energy and thermal energy, or a combined treatment energy of the ultrasonic energy and RF energy may be applied from the probe 15 to body tissue.

The movable handle 23 is rotatably attached to the housing 17. By bringing the movable handle 23 towards or away from the grip portion 20, the doctor can move the movable pipe 27 forward and backward inside the sheath 24 to open and close the jaw 26.

The sheath 24 is formed in a cylindrical shape with, for example, a metallic material and protects the probe 15 located therein. The proximal direction C2 side portion of the sheath 24 is rotatably attached to the housing 17 with respect to the housing 17. The knob 25 is fixed to the sheath 24 and is rotatably attached to the housing 17. By rotating the knob 25 with respect to the housing 17, the sheath 24, the probe 15, an ultrasonic oscillator 41, and the jaw 26 can be integrally rotated around the longitudinal axis C (central axis).

As shown in FIG. 3, the vibration generator 21 includes an ultrasonic oscillator 41 and a horn member 42. The ultrasonic oscillator 41 includes a plurality of piezoelectric elements 43 (for example, four) that change a current into ultrasonic vibrations. The ultrasonic oscillator 41 is connected to one end of an electric wire 44. The electric wire 44 passes through the inside of the cable 14, and is connected, at the other end, to the ultrasonic current supply section 35 of the power supply unit 13. When electric power is supplied from the ultrasonic current supply section 35 to the ultrasonic oscillator 41 via the electric wire 44, ultrasonic vibrations are generated in the ultrasonic oscillator 41. The vibration generator 21 can transmit the ultrasonic vibrations to the probe 15 side to produce resonance. The frequency of the ultrasonic vibrations generated by the vibration generator 21 is, for example, 47 kHz, and is a frequency not less than 46 kHz and not more than 48 kHz in an embodiment.

As shown in FIG. 3, the ultrasonic oscillator 41 is attached to the horn member 42. The horn member 42 is made of a metallic material. The horn member 42 includes a substantially conical cross-section changing portion where the cross-sectional area decreases in the distal direction C1 of the probe 15. The amplitude of the ultrasonic vibrations generated at the ultrasonic oscillator 41 is amplified in the cross-section changing portion.

As shown in FIG. 2, the jaw 26 is supported by a support pin 45 provided at a sheath 24 distal end portion. The jaw 26 is rotatable around the support pin 45 between a contact position where the jaw 26 is in contact with or approaches to face the probe 15 and a distant position where the jaw 26 is distant from the probe 15. The jaw 26 is made of a metallic material (such as titanium alloy).

Figure 4:
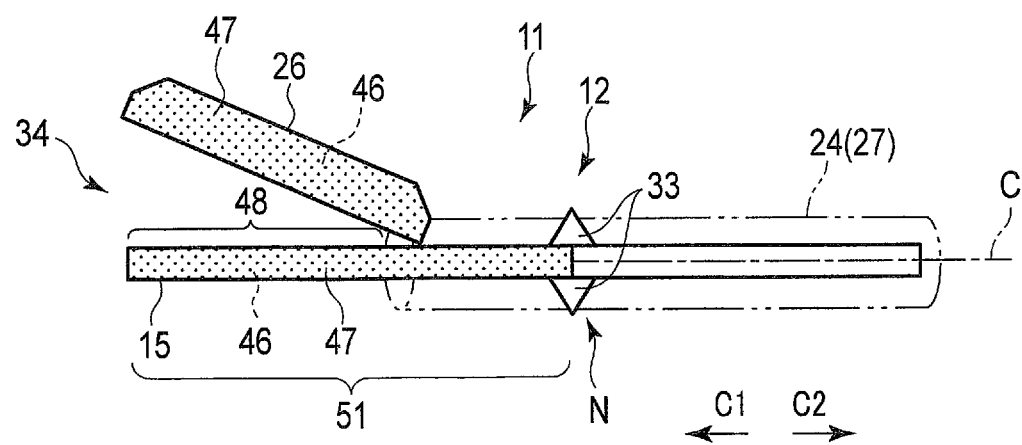
FIG. 4 is a schematic diagram schematically showing the end effector, sheath, etc. of the surgical instrument shown in FIG. 1.

As shown in FIG. 4, a film 46 made of amorphous titanium oxide (TiO, $TiO_2$) is formed on the entire surface (entire circumference) of the jaw 26. Therefore, the jaw 26 includes an amorphous titanium oxide film 46 on the surface of a metallic base material made of, for example, titanium alloy. The jaw 26 further includes a film resin 47 (resin layer) to be described later, i.e., a coating, on the film 46.

The probe 15 is made of a metallic material (such as titanium alloy). The probe 15 includes a substantially-flat treatment surface 48 at a position facing the jaw 26, and can perform various treatments on body tissue mainly by the treatment surface 48. A film 46 made of amorphous titanium oxide (TiO, $TiO_2$) is formed on the entire surface (entire circumference) of a distal portion 51 of the probe 15. Therefore, like the jaw 26, the probe 15 includes an amorphous titanium oxide film 46 on the surface of a metallic base material made of, for example, titanium alloy. The probe 15 further includes a film resin 47 (resin layer) to be described later, i.e., a coating, on the film 46. Here, the distal portion 51 of the probe 15 is, for example, the distal end direction C1 side portion of the probe 15 closer to the distal end than the position where the seal member 33 is disposed, and the distal portion 51 includes an exposed portion projecting from the distal end of the sheath 24. Hydroxyl groups (—OH groups) are apt to be formed on the surface of the amorphous titanium oxide film 46; therefore, a large number of hydroxyl groups are provided thereon.

As shown in FIG. 4, the film resin 47 covers the entire jaw 26 and the distal portion 51 of the probe 15. The resin 47 is made of a material, such as fluororesin, that prevents heated body tissue from sticking thereto. More specifically, the fluororesin is composed of, for example, PTFE, PFA, or the like. The fluororesin has water repellency and oil repellency. In addition, a molecule having a molecular structure having a functional group bonded to a hydroxyl group (silane coupling agent as one example) is mixed in this resin 47 (sticking prevention coat).

A covalent bond, which is a chemical bond, is formed between the silane coupling agent molecules and the large number of hydroxyl groups present on the surface of the film 46 of the jaw 26 and the probe 15. The resin having a molecular structure with a property of bonding to a hydroxyl group is not limited to the resin in which a silane coupling agent is mixed. For example, the resin 47 may be composed of a resin having a molecular structure with a property of bonding to a hydroxyl group other than the silane coupling agent, or a resin into which a molecule with such a property of bonding to a hydroxyl group is mixed.

Subsequently, operations performed by the surgical instrument 11 of the present embodiment and effects of the surgical instrument 11 will be described. For example, the doctor holds the handpiece 12 of the surgical instrument 11 in his or her hand, and draws the movable handle 23 to the grip portion 20 side with a finger so as to rotate the jaw 26 to come into contact with or face, with a small gap therebetween, the treatment surface 48 of the probe 15. When there is body tissue between the jaw 26 and the treatment surface 48, the treatment surface 48 and the jaw 26 can hold the body tissue therebetween like forceps. By returning the movable handle 23 to its original position, the jaw 26 moves away from the treatment surface 48, and the body tissue can be released. Moreover, when the doctor pushes in the first button 31 or the second button 32 with a finger, the controller 36 controls the ultrasonic current supply section 35 to turn on the output of ultrasonic vibrations from the ultrasonic oscillator 41, whereby an ultrasonic energy (or another energy in the case of using another energy as the treatment energy) can be input from the probe 15 to body tissue. By releasing the push of the first button 31 or the second button 32, the doctor can turn off the output of ultrasonic vibrations from the ultrasonic oscillator 41 to stop the input of the ultrasonic energy (or another energy).

In the present embodiment, the film 46 made of amorphous titanium oxide is formed on the surface (entire circumference) of the jaw 26 and the distal portion 51 of the probe 15. Many hydroxyl groups are produced on the surface of this amorphous titanium oxide film 46. Furthermore, a strong chemical bond (covalent bond) is formed between the hydroxyl groups and the silane coupling agent contained in the resin 47. Therefore, in the present embodiment, the adhesive strength of the resin 47 to the film 46 is high, and the resin 47 does not easily fall off (or peel off).

A method of manufacturing the end effector 34 of the present embodiment will be described. The end effector 34 (the jaw 26 and the distal portion 51 (including the exposed portion) of the probe 15) is dipped in an electrolyte solution, and the electrolyte solution is electrified by using the end effector 34 as an anode. The end effector 34 is anodized via electrification for a predetermined period of time to form the film 46 on the surface of the jaw 26 and the surface of the distal portion 51 of the probe 15. At this time, the electrolyte solution, electrification time, and voltage used for anodization are set to predetermined conditions; therefore, titanium oxide (TiO, $TiO_2$) is formed in the film 46 to be distributed in a non-crystalline state. Consequently, a so-called amorphous titanium oxide film 46 can be formed on the surface of the end effector 34. Alternatively, an end effector 34 in which an amorphous titanium oxide film 46 is formed can be commercially obtained by placing an order with a plating processing company having know-how for forming amorphous titanium oxide.

Amorphous titanium oxide, which is different from titanium oxide in the ordinary crystalline state, can be identified as amorphous by, for example, X-ray diffraction (XRD) and electron spectroscopy for chemical analysis (ESCA). The method of identifying amorphous titanium oxide is not limited to this, and other general structural analysis methods may be used.

A test to evaluate durability of the resin 47 (sticking prevention coat: fluororesin) was conducted using the surgical instrument 11 of the present embodiment. In this test, for example, thin-film tissue (body tissue) of an animal having a thickness of 3 mm or less, and purchased from a meat trader, was coagulated and incised using an ultrasonic energy under a predetermined condition, and evaluated for whether the thin-film tissue sticks to the probe 15 after incision. In this evaluation, for example, two points were awarded if the thin-film tissue does not stick at all, one point was awarded when the thin-film tissue sticks to an allowable extent, and zero points were awarded when the thin-film tissue sticks to the same extent to the case where the sticking prevention coat was not applied, and the resin was evaluated as "acceptable" when the average score was equal to or higher than a predetermined score. As a comparative example, one using ordinary titanium oxide as the film 46 of the jaw 26 and the probe 15 was adopted. Consequently, the surgical instrument of the comparative example did not exhibit the sticking prevention effect and failed after about 1,000 coagulations and incisions. Therefore, the durable number of the comparative example is about 1,000. On the other hand, the surgical instrument 11 of the embodiment did not exhibit the sticking prevention effect and failed after about 1,500 coagulations and incisions. Therefore, the durable number of the surgical instrument 11 of the embodiment is about 1,500. Accordingly, the durability of the sticking prevention coat was improved by 50% in the surgical instrument 11 of the present embodiment in comparison with the comparative example. Therefore, it can be understood that the adhesive force (bonding force) between the film 46 of the jaw 26 and the probe 15 and the resin 47 has increased and, as a result, the durability of the resin 47 (coating) has dramatically improved in the surgical instrument 11 of the present embodiment in comparison with the case in the comparative example.

According to the first embodiment, the surgical instrument 11 includes an end effector 34 with a surface made of amorphous titanium oxide, and a film resin 47 covering the surface and chemically bonding to the surface. With this configuration, the film resin 47 chemically bonds to the amorphous titanium oxide surface; therefore, the bonding strength can be improved in comparison with conventional adhesion by utilizing intermolecular force between molecules by physical intimate contact. Accordingly, a surgical instrument 11 including a highly-durable end effector 34 in which the resin 47 does not easily peel off can be provided.

The base material of the end effector 34 is made of metal. This configuration can facilitate adhesion of resin, which is an organic material, to metal, which is an inorganic material, which was originally difficult to achieve.

The base material is titanium alloy. This configuration can improve the adhesive strength of the film resin 47 to titanium alloy, and can provide the end effector 34 with various properties, such as a property of sticking less to body tissue, a heat insulating property, water repellency, and an insulating property.

The surface is provided on the treatment surface 48 for treating body tissue. This configuration enables bonding of the film resin 47 to the treatment surface 48 of the end effector 34. Accordingly, the treatment surface 48 can be provided with, for example, a property of sticking less to body tissue and water repellency, whereby a surgical instrument 11 including an end effector 34 which can be easily used by the doctor can be realized.

The resin 47 has a property of bonding to hydroxyl groups present on the surface. According to this configuration, the resin 47 is composed of a molecule having a functional group chemically bonding to a hydroxyl group, or contains such a molecule. Therefore, a surgical instrument 11 having an improved adhesive strength of the resin 47 to the surface of the end effector 34 can be provided.

The resin 47 contains a silane coupling agent. According to this configuration, a covalent bond is formed by a dehydration condensation reaction between the hydroxyl groups present on the surface and the resin 47. Therefore, the bonding strength can be significantly improved in comparison with conventional adhesion utilizing intermolecular force by physical intimate contact. Accordingly, a surgical instrument 11 including a highly-durable end effector 34 in which the resin does not easily peel off can be provided.

Subsequently, the surgical instrument according to modifications of the present embodiment will be described with reference to FIG. 5. In the following modifications, the parts which differ from those of the above-described embodiment will be mainly described, and descriptions of the parts identical to those of the above-described embodiment will be omitted.

The surgical instrument 11 of the first modification is identical to that of the above-described embodiment in that adhesion between the surface of the end effector 34 and the resin 47 is achieved by utilizing a covalent bond between amorphous titanium oxide (hydroxyl group) and a silane coupling agent contained in the resin 47. However, in the first modification, the film resin functions differently at different parts of the end effector 34.

A film 46 made of amorphous titanium oxide (TiO, $TiO_2$) is formed on the entire surface (entire circumference) of the jaw 26. As shown in FIG. 5, the same resin 47 (sticking prevention coat: fluororesin such as PTFE or PFA) as the one used in the embodiment is provided on the film 46 of the jaw 26 at a portion facing the probe 15. The jaw 26 includes a heat-insulating second resin 52 having smaller heat conductivity than metal on the opposite side of the portion facing the probe 15. The second resin 52 may be composed of, for example, resin (PEEK) having a general composition in which a silane coupling agent is mixed, but may also be formed by providing the resin 47 (sticking prevention coat) with a predetermined thickness or more. In general, the thickness of the second resin 52 is greater than the thickness of the resin 47. Different thicknesses for the resin 47 and the second resin 52 can be easily realized, for example, by varying the number of resin applications between the resins. The second resin 52 may also be one with an improved heat insulating property made by mixing hollow glass particles or the like in base material resin (such as PEEK) to form bubbles in the resin.

The film 46 made of amorphous titanium oxide (TiO, $TiO_2$) is formed on the entire surface (entire circumference) of the distal portion 51 (including the exposed portion) of the probe 15. As shown in FIG. 5, the probe 15 includes the same resin 47 (sticking prevention coat) as that of the embodiment on the treatment surface 48. The distal portion 51 of the probe 15 includes a heat-insulating second resin 52 on the portion opposite to the treatment surface 48 and on the portion closer to the portion of proximal end direction C2 side than the treatment surface 48. The second resin 52 may have the same composition and structure as the second resin 52 on the jaw 26 side, for example.

In the surgical instrument 11 of the second modification, two types of energies, i.e., an ultrasonic energy using ultrasonic vibrations and a high-frequency energy using a high-frequency current, are used as treatment energies to be input from the end effector 34 to body tissue. Therefore, in the second modification, the power supply unit 13 is provided with a high-frequency energy supply section that supplies a high-frequency energy to the end effector 34, in addition to the ultrasonic current supply section 35. At this time, the probe 15 of the end effector 34 is used as one pole of the bipolar-type electric scalpel, and the jaw 26 of the end effector is used as the other pole of the bipolar-type electric scalpel.

In the second modification, a film 46 made of amorphous titanium oxide (TiO, $TiO_2$) is formed on the entire surface (entire circumference) of the distal portion 51 of the probe 15 and the jaw 26, as in the first modification. As shown in FIG. 5, the same resin 47 (sticking prevention coat: fluororesin such as PTFE or PFA) as the one used in the embodiment is provided on the film 46 of the jaw 26 at a portion facing the probe 15. The jaw 26 includes a second resin 52 having an insulating property and a heat insulating property on the opposite side of the portion facing the probe 15. The second resin 52 may be composed of, for example, resin (PEEK) having a general composition in which a silane coupling agent is mixed, but may also be formed by providing the resin 47 (sticking prevention coat) with a predetermined thickness or more. In the second modification, it is preferable to make the thickness of the second resin 52 larger than that in the first modification in order to ensure a sufficient insulating property.

Figure 5:
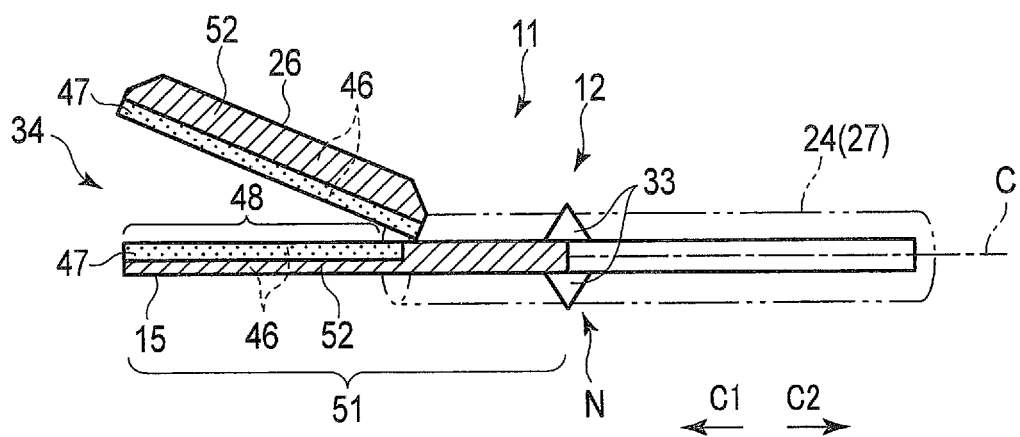
FIG. 5 is a schematic diagram schematically showing the end effector, sheath, etc. of the surgical instrument according to the first and second modifications.

As shown in FIG. 5, the probe 15 includes the same resin 47 (sticking prevention coat) as that of the embodiment on the treatment surface 48. The distal portion 51 of the probe 15 includes an insulating and heat-insulating second resin 52 on the portion opposite to the treatment surface 48 and on the portion closer to the portion of proximal end direction C2 side than the treatment surface 48. The second resin 52 may have the same structure and composition as the second resin 52 on the jaw 26 side, for example.

According to the first modification and the second modification, the surgical instrument 11 includes a film second resin 52 covering the surface, chemically bonding to the surface, and having a different function from the resin 47. This configuration enables appropriate setting of the type, property, and function of the resin according to the application/specification. Thus, for example, resins (resin 47 and second resin 52) having different functions can be applied to different parts of the end effector 34. Accordingly, the degree of freedom of design can be improved, and a surgical instrument 11 with improved convenience for the doctor and improved safety can be provided. In particular, according to the first modification in which the heat-insulating second resin 52 is provided, thermal invasion to the surrounding tissue can be reduced by the second resin 52. According to the second modification in which the insulating and heat-insulating second resin 52 is provided, the second resin 52 can prevent a high-frequency current from leaking out to the surroundings, thereby preventing the high-frequency current from exerting an adverse effect on the surrounding tissue.

The present invention is not limited to the above-described embodiment, and can be appropriately modified in practice, without departing from the gist of the invention. In the above-described embodiment and modifications, titanium alloy is used as the metal base material of the jaw 26 and the probe 15, and amorphous titanium oxide (TiO, $TiO_2$) is used as the coating film 46; however, the metal base material of the jaw 26 and the probe 15 is not limited thereto. For example, aluminum alloy may be used as the metal base material of the jaw 26 and the probe 15, and amorphous aluminum oxide ($Al_2O_3$) may be used as the coating film 46. Even in this case, a large number of hydroxyl groups are provided on the surface of the film 46, and a resin coating that does not easily fall off can be realized owing to the chemical bond (covalent bond) between the hydroxyl groups and the resin 47. Furthermore, it is as a matter of course possible to realize one surgical instrument by appropriately combining the surgical instrument 11 of the embodiment and those of the first modification and the second modification.

The surgical instrument 11 according to another example of the present invention will be described below.

[1] A surgical instrument comprising:
an end effector with a surface made of amorphous oxide; and
a film resin covering the surface and chemically bonding to the surface.

[2] The surgical instrument according to [1], wherein a base material of the end effector is made of metal.

[3] The surgical instrument according to [2], wherein the base material is aluminum alloy.

[4] The surgical instrument according to [3], wherein the oxide is aluminum oxide.

[5] The surgical instrument according to [2], wherein the base material is titanium alloy.

[6] The surgical instrument according to [5], wherein the oxide is titanium oxide.

The invention claimed is:

1. A surgical instrument comprising:
an end effector,
a treatment surface (1) configured to treat body tissue and (2) on the end effector,
an amorphous oxide membrane/film/coat covering the treatment surface of the end effector,
a hydroxyl group on a surface of the amorphous oxide membrane/film/coat, and
a resin covering the surface of the amorphous oxide membrane/film/coat,
the resin the surface of the amorphous oxide membrane/film/coat, the resin is chemically bonded to the hydroxyl group.

2. The surgical instrument according to claim 1, wherein the end effector includes a distal portion that treat is configured to treat the body tissue by an ultrasonic vibration, and a jaw rotatably attached, and
the treatment surface is formed in the distal portion.

3. The surgical instrument according to claim 2, further comprising a pipe and a seal member, wherein:
the end effector includes a probe that (1) transmits an ultrasonic vibration along a longitudinal axis and (2) is partially housed in the pipe;
the seal member is operatively between the probe and the pipe; and
the resin is formed at a side closer to a distal end of the probe than to the seal member.

4. The surgical instrument according to claim 2, wherein the probe and the jaw are configured to pass a high-frequency energy.

5. The surgical instrument according to claim 1, wherein the amorphous oxide film is titanium oxide.

6. The surgical instrument according to claim 1, wherein the resin is provided with the property of bonding to a hydroxyl group by mixing a silane coupling agent in the resin.

7. The surgical instrument according to claim 1, wherein the resin is fluororesin.

8. A surgical instrument comprising:
an end effector,
a treatment surface for treating body tissue, provided on the end effector,
an amorphous oxide membrane/film/coat covering the treatment surface of the end effector, and
a resin covering the amorphous oxide membrane/film/coat, the resin having a property of bonding to a hydroxyl group, wherein
the end effector includes a distal portion that treats the body tissue by an ultrasonic vibration, and a jaw rotatably attached,
the treatment surface is formed in the distal portion, and
a surface of the distal portion opposite to the treatment surface is further coated with a heat-insulating second resin.

9. The surgical instrument according to claim 8, wherein the second resin contains a hollow glass particle to have an improved heat insulating property.

10. The surgical instrument according to claim 8, wherein the second resin is thicker than the resin.

11. A surgical instrument comprising:
an end effector,
a treatment surface for treating body tissue, provided on the end effector,
an amorphous oxide membrane/film/coat covering the treatment surface of the end effector, and
a resin covering the amorphous oxide membrane/film/coat, the resin having a property of bonding to a hydroxyl group, wherein
the end effector includes a distal portion that treats the body tissue by an ultrasonic vibration, and a jaw rotatably attached,
the treatment surface is formed in the distal portion, and
the jaw includes a surface of the amorphous oxide membrane/film/coat and the resin having the property of bonding to the hydroxyl group is covering the surface.

12. A surgical instrument comprising:
an end effector with a surface of an amorphous oxide membrane/film/coat;
a hydroxyl group on an outer surface of the amorphous oxide membrane/film/coat; and
a film resin covering the hydroxyl group that is chemically bonded to the hydroxyl group.

13. A probe comprising:
a vibration transmission member made of titanium alloy configured to treat body tissue by an ultrasonic vibration;
a membrane/film/coat made of amorphous titanium oxide on a distal side of the vibration transmission member;
a hydroxyl group on an outer surface of the membrane/film/coat; and
a film resin on the membrane/film/coat in which a molecule having a molecular structure having a functional group chemically bonding to the hydroxyl group is mixed.

* * * * *